(12) United States Patent
Xu

(10) Patent No.: US 7,026,005 B2
(45) Date of Patent: Apr. 11, 2006

(54) PROCESS FOR TEA FLOWER

(76) Inventor: Jiying Xu, No. 6-102, Jing Ting Yuan B District, XuanCheng City, AnHui Province (CN) 242000

( * ) Notice: Subject to any disclaimer, the term of this patent is extended or adjusted under 35 U.S.C. 154(b) by 38 days.

(21) Appl. No.: 10/486,502

(22) PCT Filed: Aug. 20, 2001

(86) PCT No.: PCT/CN01/01229

§ 371 (c)(1),
(2), (4) Date: Aug. 16, 2004

(87) PCT Pub. No.: WO03/015529

PCT Pub. Date: Feb. 27, 2003

(65) Prior Publication Data

US 2004/0258813 A1    Dec. 23, 2004

(51) Int. Cl.
*A23F 3/00*    (2006.01)
(52) U.S. Cl. ...................... 426/597; 426/615
(58) Field of Classification Search ............... 426/597, 426/615
See application file for complete search history.

(56) References Cited

FOREIGN PATENT DOCUMENTS

| CN | 1052994A | A | 7/1991 |
|---|---|---|---|
| JP | 62166846A | A | 7/1987 |
| JP | 62-232363 | * | 10/1987 |
| JP | 02-69143 | * | 3/1990 |
| JP | 2069143A | A | 3/1990 |
| JP | 2167031A | A | 6/1990 |

OTHER PUBLICATIONS

Derwent Abstract. Acc. No. 2003-394326. CN 1399894. Published Mar. 5, 2003. Inventors: Dong et al.*
JPO Abstract for JP361280255A. Published Dec. 10, 1986. Inventor: Saito.*
Derwent Abstract Acc. No. 2001-497444. CN 1296762. Published May 30, 2001. Inventor: Lui.*
Derwent Abstract Acc. No. 2001-528082. KR 368634. Published Jan. 24, 2003. Inventors: Kim et al.*
Derwent Abstract Acc. No. 1999-508056. CN 1220096. Published Jun. 23, 1999. Inventors: Du et al.*

* cited by examiner

*Primary Examiner*—Anthony Weier
(74) *Attorney, Agent, or Firm*—Venable LLP; Ann S. Hobbs

(57) ABSTRACT

The present invention relates to a method for processing tea tree product, in particularly, a method for processing tea flower. The process comprises of the following steps: picking, dehydrating, steaming, drying, quick-freezing and pulverizing of the tea flowers. The whole production process is conducted in a natural way and no chemical reaction or chemical extraction is involved. Therefore natural nutrients and different kinds of effective ingredients of the tea flowers could be preserved to a maximum degree.

3 Claims, No Drawings

PROCESS FOR TEA FLOWER

FIELD OF THE INVENTION

The present invention relates to a method for processing tea tree product, in particularly, a method for processing tea flower.

BACKGROUND OF THE INVENTION

Tea is the earliest pure natural beverage and China is the earliest country that developed and utilized the tea resource in the world. Based on the researches on tea drinking and the physiological effect of the extracts from the tea, it is indicated that tea possesses the function of detoxicating, plasma lipid levels lowering, senility resisting and cancer resisting and inhibiting. The main ingredient that produces these functions is tea polyphenols. Tea polyphenol is one of the main active ingredients in tea, possessing specific strong oxidizing action. It is a kind of most ideal natural oxide-resistant agent and has wide applications in animal and vegetable oils, foodstuff, beverage, aquatic products, dairy products, candy, medical health care products and the like.

Tea flower is the reproductive organ of tea tree. Due to its long growth period, large amount of organic substances are accumulated in its body, especially the contents of tea polyphenols, amino acids, proteins, tea polysaccharides and saponins are very high; In the past, people planted tea tree and consumed tea, and neglected, however, the research and application of tea flower, because it was generally believed that blossoming and bearing fruits of the tea tree are only for the purpose of reproduction. In reality, asexual reproduction techniques have already been applied for the reproduction of tea tree in China. The percentage of fruit and seed of tea tree used nowadays for reproduction purpose is very low and blossoming and bearing fruit are therefore only a heavy burden for the tea tree because it takes 18–20 months for the tea tree to allow differentiation of blossom bud to ripening of tea seed. In this interval of growth period, tea trees blossom while bearing seeds and gestating new lives. Tea flowers compete with buds and leaves for more water, fertilizer and nutrients in their long growth period. The flower and fruit of the preceding year together with the flower of the present year amount to 45–55% of the total flower bud. Such over-prosperous reproductive growth severely inhibits nourishment growth and will results in certain unfavorable effect on the quality of the tea produced. In order to terminate the reproductive growth of the tea tree, tea flowers are picked off manually. Thus, it is feasible to turn the unutilized waste of the past 5000 years into valuable product as well as to raise the productivity and quality of the tea flower.

Tea flowers, the essence of tea tree, begin to bud in very warm season and blossom in frost season. Its flower is white, light yellow and pink in color. The diameter of the flower is 4–9 mm and the petal of the flower is either single lobe or multi lobe and is generally composed of pentagon to enneagon shaped petals. Tea flower is a kind of bisexual flower exhibiting cross-pollination. There are 200–300 androeciums in the petal. Pistils are situated in the center of the androecium. The ripened tea flowers could secrete honeydew having attractive fragrance.

Although tea flowers have a long growth period, they are quite tender. Selecting and picking the tea flowers and then transporting them and processing them into products seem to be a simple and yet complicated productive processing course. In these multiple processing steps, it seems to be quite simple, there are, however, contain many scientific requirements. If any of the steps is not operated according to rigorous technique, the active substance of the tea flower will possibly be dissipated and evaporated and thus will render the flower to be a waste having only externality but no active ingredient. Tea flower is the essence of the tea and the purpose of the picking of the flower is to obtain the essence of the tea. To retain the ingredients of the tea flower to a maximum degree in the productive processing steps, the key seems to rely solely on the proper handling of the productive processing and on the properly applying science to producing techniques. For the moment, there is no report on the processing method of tea flower in prior art.

THE OBJECTIVE OF THE INVENTION

Based on the above-mentioned understanding, the objective of the present invention is to develop a practical and effective method for processing tea flowers and their product.

The inventor of the present invention was born in an old and well-known family of tea producer and was graduated from the Department of Tea Science, Agricultural University of Anhui. Based on practical experiences accumulated in many years on tea production and research, productive processing of tea flowers as well as repeated investigation and demonstration, the inventor complete the present invention.

The objective of the present invention is to provide a method for processing tea flowers and their product. The said process is full of techniques, rigorous in technology and simple and practical. The products generated from the said process include fresh tea flower, dried flower, pollen, tea flower powder and the like. They have wide applications in the fields of medical health care, foodstuff, beverage, cosmetics, women and children articles, textile industry and chemical engineering industry.

THE CONTENT OF THE INVENTION

The objective of the present invention could be realized in the following way. The process comprises the following steps: picking, dehydrating, steaming, drying, quick-freezing and pulverizing of the tea flowers. The picking step is preferably carried out in the time interval beginning from 2–3 days before the pollination of the tea flower to 2–3 days after the pollination of the tea flower. Hollow baskets made of bamboo or plastics are used to accommodate the picked tea flowers during the picking and the said tea flowers must be immediately graded and spread. In the dehydrating step, the said tea flowers should be spread at a thickness of 2–5 cm on bamboo mat or cement floor and should be gently turned over once every 1 hour. The time of dehydrating for the spread fresh flowers does not exceed 10 hours and the most preferred spreading time is 6 hours. Having been dehydrated, the tea flowers are steamed. A steamer for tea preparation is used directly and the temperature heating the flowers is controlled in a range of 80–100° C.; The drying step is carried out in several times and most preferably in 3–4 times. The temperature of drying is controlled in a range of 60–180° C. The thickness of the flower on the baking plate of the dryer is in the range of 2–3 cm. After every drying, the tea flowers are taken out of the dryer and spread until cool. The time for spreading cool should be getting longer and longer each time. In the quick-freezing step, the tea flowers are quick-frozen at −20° C. to −40° C. for 20 minutes. In the pulverizing step, the quick-frozen flowers are taken out of the freezer and immediately put into pulverizer to be pulverized.

ADVANTAGES OF THE INVENTION

The whole production process is conducted in a natural way and no chemical reaction or chemical extraction is involved. Therefore natural nutrients and different kinds of effective ingredients of the tea flowers could be preserved to a maximum degree.

EMBODIMENTS OF THE INVENTION

1. Picking of flower: The quality of the tea flower and its product firstly depends on the raw material, tea flower. Therefore there is a rigorous criterion for the fresh tea flower.
    a) The blossoming time of the tea flower will vary from place to place. Generally tea tree begins to blossom from October this year to January next year.
    b) The criterion for fresh flower: The fresh flowers of the tea tree that contain more than 8% of tea polyphenol could be used. It is generally acknowledged that tea tree bud and petal just leaving the stamen or pistil of a flower could be picked 2–3 days before and after the pollination. These are very energetic flower with unfaded petal. For those flowers whose petals already fade should not be picked. During the picking, it is advised to pick and put them in a careful manner to keep the flower complete in shape and keep stamen or pistil not fall off or only least fall off. Ventilative hollow baskets or crates of environmental protection type made of bamboo or plastics are used to accommodate the picked tea flowers during the picking. The amount put in the vessel should not exceed 3 kilograms. For those large crates used in tea field, the maximum amount of storing should not exceed 25 kilograms. This measure is taken to prevent possible suffocation of the tea flowers piled at the lower portion of the vessel. The fresh flowers are graded batch by batch when they are transported to the initial treating field and are instantly spread on bamboo mat or cement ground. When the flowers are wetted with dew, they should be dehydrated to remove the water at the surface before spreading. The flowers are spreaded to a thickness of not more than 2–5 cm to effectively expel the humidity and moisture. The spread flowers should be gently turned over once every 1 hour to allow dehydration in natural atmosphere to an extent of 10%–15% in the course of spreading before the commencement of the second step.
2. Freshness-kept-flowers: Freshness-kept-flowers are picked under more rigorous criterion. They should be large with complete corolla. Those with 7–9 mm multipetal are selected while those welted with dew are not selected. Other picking criterions are identical with those mentioned in the preceding paragraph; Freshness-kept-flowers are picked with proper choice. In addition, they are subjected to another careful choice after dehydration. Then they are spread. When their breath stops and the natural dehydration reaches 5%–8%, they are packed into bags at amount of 50 g–100 g and the bags are evacuated to remove oxygen and then filled with nitrogen. Finally the bags are packed into boxes at the amount of 50–200. The boxes are moved to storehouse where the temperature is kept at 2° C.–8° C. The storehouse should be clean, hygienic and ventilated.
3. Flower drying: The raw materials for dried flowers are identical to those of freshness-kept-flowers. Their processing includes dehydration→steaming→drying (divided into 4 times). When the loss of water of the spread flowers reaches 10%–15%, steaming step starts. It is most preferred to use steamer of model 60K, 120K, 180K and iron steamer. When steamer 120K is used, 0.2 kilogram atmospheric pressure should be used, the temperature heating the flower should reach 80° C.–100° C. and the amount of flower spread and steamed should be 200 kg–250 kg per hour. The steaming step could be terminated when the petal fade and the color of the flowers are darker than those of fresh flowers. The steamed flowers are then taken out of the steamer and spread to cool. In the steaming step, polyphenol oxidized enzymes are removed and the water contents at the surface layer of the flower are increased. However effective ingredients and water in the flowers are not decreased. For the sake of preventing the dissipation and change of the effective ingredients in the flower, they are not turned over during spreading. After 1 hour, depending on the extent of evaporation of the water at the surface layer, the succeeding step could start. The drying step could be carried out in 4 times. Dryers of model 10, 14, 16 and thermoscreen are most preferred. Fuels used could be wood, coal, natural gas etc., but sunlight should not be used (it could influence the stability of the effective ingredients). In case of using dryer model 16K, beginning from the first time to the fourth time, the temperature is in the range of 60° C.–180° C. and the most preferred temperature is 100° C. Too low temperature of drying will influence the efficiency of drying while too high temperature will influence the nutrients of tea flowers. The thickness of the tea flower on the baking plate should be in the range of 2–3 cm. The drying temperature could be lowered along with the decrease of the water content in the flower and the thickness of the flower to be dried could be thickened along with the decrease of the water content. The water content could approximately be lowered as follows; 70%→50%→30%→8%→5%. During the intervals of drying steps, depending on the water content, the flowers being dried should appropriately be spread to cool. Time for spreading to cool is respectively 1–2 hours, 2–3 hours, 3–4 hours and 40 hours (for the last time) and only after spreading to cool, the drying could be carried on. The thickness of the spread flowers is in the range of 3–10 cm and could be thickened along with the decrease of water content. In the whole course of drying, it is rigorously required to handle the dialectical relationship among "temperature, amount of flower and drying time" to control water content of the flowers. Handling this dialectical relationship skillfully is the key point for controlling the effective ingredients. The final products of dried flowers are packed in amount of 10 kg–20 kg into environmental benign boxes with inner and outer double layer packages. They are stored in freshness-keeping-storehouse at 2° C.–10° C. 50 g–100 g dried tea are packed in small gift boxes and in simple bags. Every 100 or 50 small gift boxes is packed into large or medium boxes and are available in the market.

4. Tea powder: The raw materials for tea powder include buds ready to bloom as well as fresh flowers that have bloomed but not yet faded. Their content of polyphenol should not be lower than 8%. Fresh tea flowers that are picked for processing into powders have to be selected manually first. Old yellow flowers, unenergetic petals and offcolored flowers should all be excluded. The selected fresh flowers are then spread. Flowers wetted by dew have to be dehydrated to remove completely the water on surface before spreading. The thickness of spreading and processing method are identical with those for dried flowers. Water content of the final dried flower is about 5%–6%. Conventional pulverizer of the closed type could be used to pulverize the said dried flowers into different size of powders at 10–3800 mesh to nanometer scale.

The processing of ultra fine powder of fresh tea flower: Upon this process, the selected tea flowers dehydrated are pulverized rapidly into ultra fine powder of tea flowers of 300 mesh or more. The products produced by such processing could retain the effective ingredients, pharmacological ingredients and intrinsic properties of the tea flowers to a maximum extent.

The processing of quick-frozen technique to tea flowers: The selected tea flowers are subjected to a quick-frozen treatment of −20° C. to −40° C. for 20 minutes and then pulverized to fine powders of tea flowers with identical quality as above-mentioned ultra fine powder processing. The nutrients and effective ingredients will not be impaired.

According to different demands, the post-processing of the present invention could also comprise the extraction of inner-contained substances of the tea flower: The selected fresh tea flowers and dried flowers are subjected to diamine extraction to get the effective ingredients of the flowers. The separation process for the tea flowers: Fresh tea flowers or dried flowers are put into separator to be separated. Thus individual species of petal, stamen or pistil, pollen and receptacle etc. are obtained. Different products could be generated from the individual species.

In view of above, the present invention provides a unique method for processing tea flower. Different products could be formed from the different steps of the said method to meet demands of different markets and consumers. Obviously the present invention is a novel, advanced and highly practical design. The above-mentioned contents are the embodiments and the technological principles involved of the present invention. It is hereby pointed out that any equivalent modifications made to the design of the present invention together with functions and actions produced therefrom that does not exceed the essence covered by the present document and attached figures are considered to be within the scope of the present invention.

What is claimed is:

1. A method for processing tea flowers, characterized in that:
   picking step, which is carried out in a time interval beginning from 2–3 days before the pollination of the tea flower to 2–3 days after the pollination of the tea flower, hollow baskets made of bamboo or plastics are used to accommodate the picked tea flowers during the picking, and the said tea flowers must be immediately graded and spread;
   dehydrating step, wherein the said tea flowers should be spread to a thickness of 2–5 cm on bamboo mat or cement ground and should be gently turned over once every 1 hour, the time of dehydrating for the spread fresh flowers does not exceed 10 hours;
   steaming step, after having been dehydrated, the tea flowers are steamed, a steamer for tea preparation is used directly and the flower is heated at a controlled temperature in a range of 80–100° C.;
   drying step, which is carried out in several times in a dryer, the temperature of drying is controlled in a range of 60–180° C., the thickness of the flower on a baking plate of the dryer is in the range of 2–3 cm, after each drying, the tea flowers are taken out of the dryer and are spread to cool, and the time for spreading to cool should be getting longer and longer each time;
   quick-freezing step, the tea flowers are quick-frozen at −20° C. to −40° C. for 20 minutes in a freezer;
   pulverizing step, the quick-frozen flowers are taken out of the freezer and immediately put into a pulverizer to be pulverized.

2. The method for processing the tea flowers according to claim 1, characterized in that the most preferred spreading time is 6 hours in the dehydrating step.

3. The method for processing the tea flowers according to claim 1, characterized in that the drying is carried for 3–4 times in the drying step.

* * * * *